United States Patent [19]

Chein

[11] 4,261,359
[45] Apr. 14, 1981

[54] CONTINUOUS INJECTION SYRINGE FOR VETERINARY USE

[76] Inventor: Ping-Hwang Chein, No. 114, Chung Hsing Rd., Ta-Lin Chin, Chia-Yi Hsien, Taiwan

[21] Appl. No.: 79,462

[22] Filed: Sep. 27, 1979

[51] Int. Cl.³ .............................................. A61D 7/00
[52] U.S. Cl. ..................................... 128/223; 128/234
[58] Field of Search ............ 128/223, 234, 224, 218 R

[56] References Cited

U.S. PATENT DOCUMENTS

| 3,682,175 | 8/1972 | Halter | 128/223 |
|---|---|---|---|
| 4,020,838 | 5/1977 | Phillips et al. | 128/223 |

FOREIGN PATENT DOCUMENTS

| 108012 | 7/1939 | Australia | 128/223 |
|---|---|---|---|
| 111309 | 9/1940 | Australia | 128/223 |

*Primary Examiner*—John D. Yasko
*Attorney, Agent, or Firm*—Tak Ki Sung

[57] ABSTRACT

A continuous injection syringe for veterinary use comprising a cylinder, a glass tube disposed within the cylinder, one end of the cylinder and tube being attached to a cylinder head having a centrally disposed orifice, the orifice being blocked and unblocked by a movable stuffing leaf, a needle base fitted over the cylinder head for the insertion of the blunt end of a hypodermic needle, a screw cap fitting over the other ends of the cylinder and glass tube, a spiral pipe being disposed through a central opening in the screw cap, a piston rod disposed within the spiral pipe, the end of the piston rod which is located within the cylinder and tube being provided with two valves and the other end being attached to a press handle, the piston rod and press handle having a hollow conduit through which liquid medicine flows, and a coil spring disposed outside the cylinder and tube, the spring urging the piston head away from the end to which the needle is attached.

2 Claims, 4 Drawing Figures

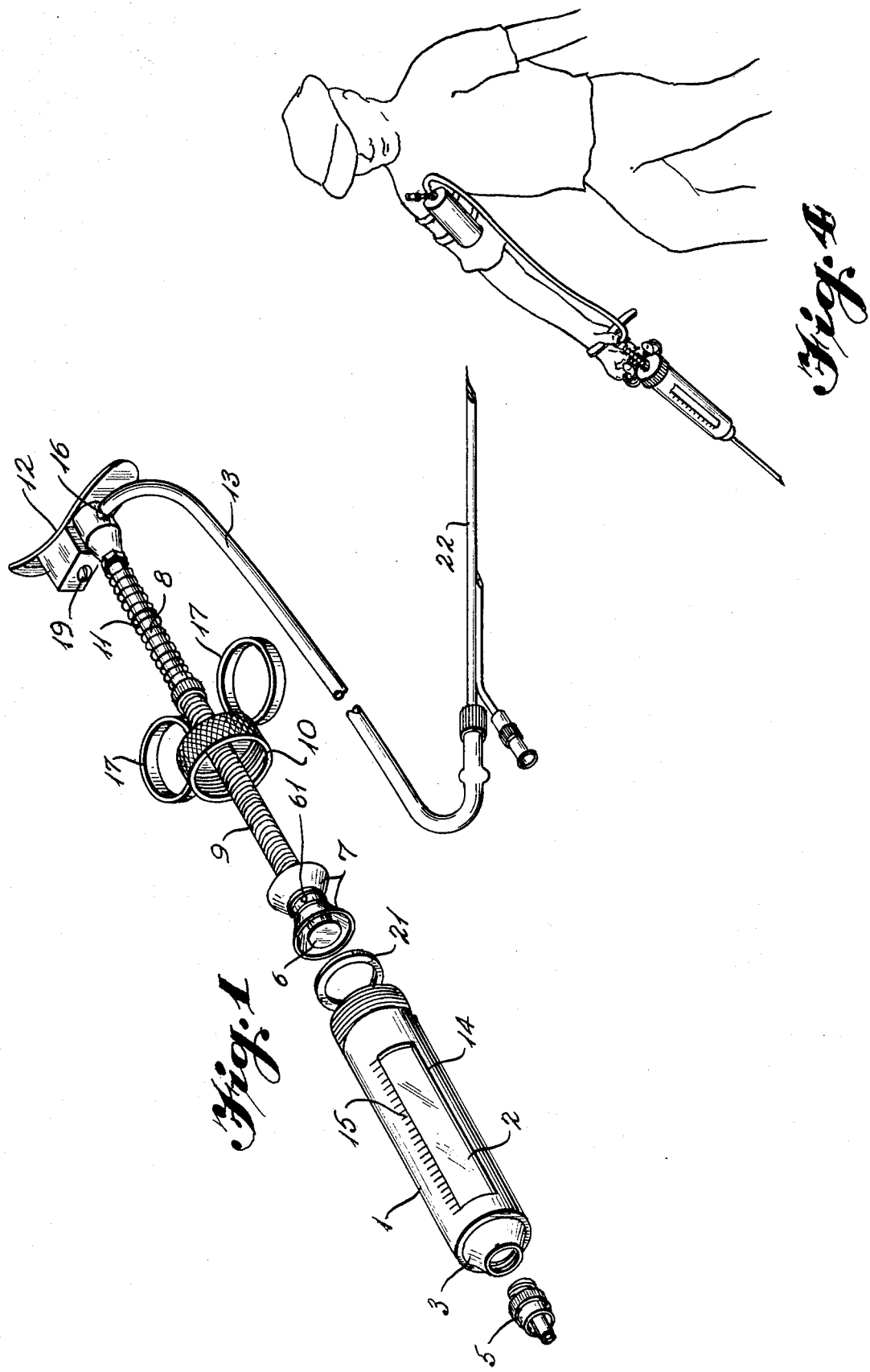

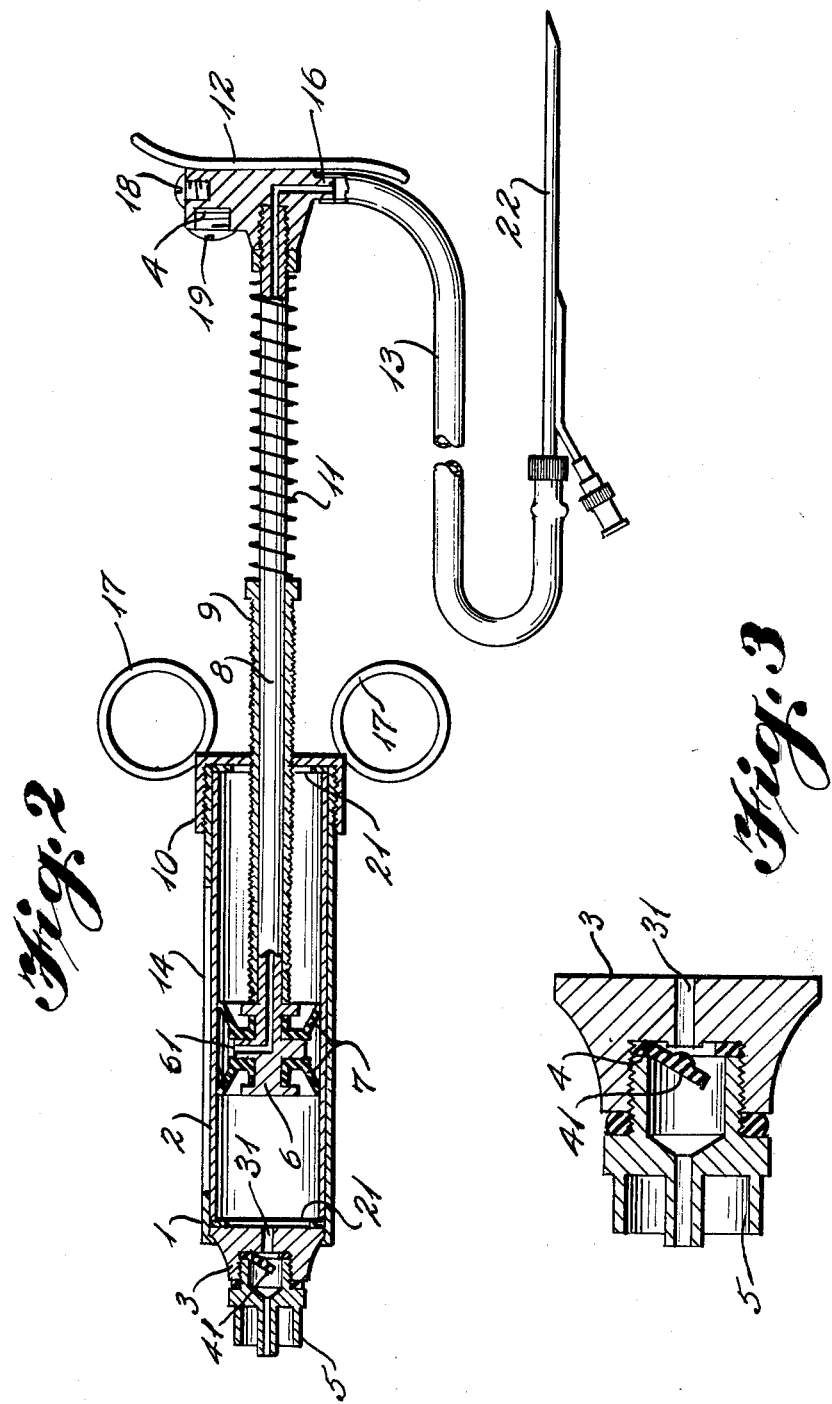

CONTINUOUS INJECTION SYRINGE FOR VETERINARY USE

This invention relates to a continuous injection syringe for veterinary use, especially related to one in which the liquid medicine is sucked into a cylinder by one-way suction, that improves certain defects present in conventional continuous type syringe with two valves for supplying a liquid medicine. Outstanding results, exact control over amount of liquid dispensed, ease of operation and dual-purpose, are provided by this invention.

Traditionally, syringes for veterinary use have many parts. When parts are damaged, the entire syringe is discarded due to difficulties in making repairs. At present, syringes are of the conventional type and the continuous type. The former is used by sucking a liquid one time and ejecting it one time. In the latter, the liquid is sucked automatically by a piston rod for continuous injection.

In the syringe of a continuous type, there are two sets of valves which consist of springs and steel balls, one is in the suction inlet which is on the side-wall of the forward end of the syringe cylinder, and the other in the needle base which is in the forward end of the cylinder. When the piston rod is pulled, the steel ball inside the forepart of the cylinder will close the injection orifice, and the steel ball inside the suction inlet escapes from an opening for sucking a liquid into the cylinder. By pressing the piston rod into the cylinder, the steel ball inside the suction inlet will stop the opening and the liquid in the cylinder will push the steel ball away from the orifice to allow the liquid to pass through to a needle. However, this continuous type can not be used as a conventional type syringe. Meanwhile, during the operation of draining and ejecting the liquid medicine, clogging and back flow of the liquid medicine occur frequently, so that deficiency and deviation of an injection amount occurs. Furthermore, a flexible hose connects the suction inlet to a bottle containing the liquid medicine which is carried on the bosom, so that the hose is necessarily quite a long one for injection to livestock. Furthermore, an injection must stop when the hose is caused to break loose by the livestock. Those above said defects are frequently experienced by veterinary surgeons.

The object of this invention is to improve the above said defects and provide a new structure of dual-purpose continuous injection syringe. The characteristics of this invention are: a liquid medicine flow through channel inside the piston rod, a suction inlet at the joint of piston rod and press handle, a movable stuffing leaf at the injection orifice, and sucking and ejecting the liquid medicine by using a rubber valve inside a cylinder, which characteristics give the present syringe excellent effects for administering medication to animals.

Since the present syringe has two rubber valves in the front of the piston rod and an outlet for the liquid medicine set between the two valves, the liquid passes through the interior or the piston rod, and the suction inlet is set at the press handle head, the operation of injection is not impeded. When a liquid medicine is sucked and ejected, clogging and back current will not occur. Furthermore, a movable stuffing leaf is provided at the injection orifice, which is used to control the ejection of the liquid medicine to produce excellent effects and decrease its cost. The defects in traditional syringes consisting of springs and steel ball, their high cost and high break-down frequency, clogging and back flow are eliminated.

Another characteristic is that because the flexible hose connecting the syringe and the bottle of liquid medicine are carried in the upper-arm, the length of the hose can be adjusted according to the length of the user's arm and the hose will not be broken loose by the livestock, the injection will not be interrupted and the liquid medicine will not be wasted. Meanwhile, the operation of injection will be easy to manage without trouble and the veterinary surgeon can raise the efficiency of the work done twice or more.

Another characteristic is that there is a screw eye adjacent the press handle for preserving a ready-screw, so that when this invention is not used as a continuous syringe, the hose is removed and the ready-screw at the suction inlet in the hose is fastened for closing up the channel. Then the movable stuffing leaf inside the front part of the cylinder is taken down for drawing the liquid medicine needed.

The details of this invention will be described with reference to the attached drawings as follows:

FIG. 1 is a perspective view of the essential parts of this invention. p FIG. 2 is a cross-sectional view of the composition of this invention.

FIG. 1 is a perspective view of the essential parts of this invention.

FIG. 2 is a cross-sectional view of the composition of this invention.

FIG. 3 is a cross-sectional view of the structure of a movable stuffing leaf inside the front part of this invention.

FIG. 4 shows the use of this invention.

The parts in FIGS. 1, 2 and 3 are: 1. cylinder, 2. glass tube, 3. cylinder head, 4. movable stuffing leaf, 5. needle base, 6. piston head, 7. rubber valve, 8. piston rod, 9. regulated spiral pipe, 10. screw cap, 11. spring, 12. press handle, and 13. flexible hose.

In the center of cylinder head 3, injection orifice 31 is provided. Orifice 31 has a movable stuffing leaf 41 for blocking and unblocking the orifice. The cylinder head 3 is screwed to needle base 5.

The groove 14 with scale divisions on the cylinder 1 is for indicating the amount of liquid medicine stored in the tube 2 and is adjusted by regulating spiral pipe 9. Inside the cylinder 1 there are provided a glass tube 2 and rubber washers 21 disposed at two ends of the glass tube. One of the washers is fixed to piston rod 8 by screw cap 10 and is screwed tight.

The piston head 6 at the end of piston rod 8 has two rubber valves 7 which form a tight seal with the wall of glass tube 2 and can slide along the longitudinal axis of the tube. On the side-wall of piston head 6 there is an outlet 61 which is connected to a liquid medicine channel 16. The piston rod 8 passes through the regulated spiral pipe 9, and fixed in cylinder 2 by screw cap 10 which regulates the distance the spiral pipe 9 can travel up and down tube 2 to the piston set in the glass division for sucking needed amount of liquid medicine. The other end of piston rod 8 is screwed to a press handle 12 and a spring 11 is provided between piston rod 8 and press handle 12. When the aforesaid piston rod is screwed onto the press handle head, liquid medicine can pass through the piston rod to the suction inlet.

Two hollow rings 17 are welded on both sides of screw cap 10 at a coordinated position for easy injection operation as illustrated FIG. 4.

When using the present syringe, injection needle is put into needle base 5 first and suction needle 22 is inserted in a liquid medicine bottle. The thumb is then placed on the press handle 12 and the rings 17 are drawn by the index finger and the little finger so that the piston rod will be moved forward by pressing down the handle. When the piston rod is pressed to the bottom and released, the piston rod 8 with rubber valve 7 will move back up by spring 11, creating a vacuum inside the cylinder 2. Because of this vacuum, injection orifice 31 will be closed by movable stuffing leaf 41 while liquid medicine is sucked through the outlet 61 into the glass tube. If the piston rod is pressed down again, the movable leaf 41 will be pushed open by liquid medicine causing the liquid medicine to be ejected. When the pressure is removed from the press handle, the liquid medicine will be sucked again from the bottle into the glass cylinder, so that the user can continuously inject constant or equal amounts of liquid medicine.

There are two screw eyes on the press handle head for preserving a ready-screw 18, 19. When the present syringe is used as a conventional syringe, the hose 13 is removed and the ready-screw at the suction inlet 16 is plugged for closing up the channel 16. Meanwhile, the movable stuffing leaf 41 inside the cylinder head should be removed and attached to screw eye 18 to prevent loss or misplacement of the leaf. An injection needle is set in a needle base which is connected to the glass cylinder so that injections in succession can be carried out by drawing the liquid medicine needed from a bottle.

In summary, the structure of the present syringe can be conveniently used in immunizing livestock.

I claim:

1. A continuous injection syringe for veterinary use comprising:
   a cylinder having a first end and a second end and a groove extending along the longitudinal axis thereof;
   a glass tube disposed within said cylinder and having a first end and a second end;
   a cylinder head attached to the first ends of the cylinder and the tube, the head having a centrally disposed orifice;
   a movable stuffing leaf disposed adjacent the orifice in the cylinder head for blocking and unblocking the orifice;
   a needle base having one end being fitted over the cylinder head and the other being adapted for the insertion of the blunt end of a hypodermic needle;
   a screw cap fitting over the second ends of the cylinder and the glass tube and having a centrally disposed threaded opening and a pair of diametrically opposed rings attached to the exterior surface of the screw cap;
   a regulated spiral pipe comprising a hollow tube and having a first end disposed within the tube and a second end disposed outside the glass tube and threads on the exterior surface thereof to engage the threads provided in the screw cap;
   a piston rod disposed within the spiral pipe, the piston rod comprising a hollow tube and having two ends, a first end disposed within the glass tube and a second end disposed outside the glass tube;
   a piston head attached to the first end of the piston rod, the piston head having a pair of valves attached thereto, the valves having a diameter which is substantially the same as the inside diameter of the glass tube and being so arranged that during longitudinal movement of the spiral pipe, one valve is open and the other is closed, the valves contacting the first end of the spiral pipe to prevent the exit of the piston rod out of the spiral pipe, the opening in the first end of the piston rod being disposed between the pair of valves;
   a press handle affixed to the second end of the piston rod, the handle being provided with a hollow conduit having two ends, the first end being connected to the opening in the second end of the piston rod and the second end being connected to a flexible hose which, in turn, is connected to a container of medication to be injected into the animal, the container being adapted to be strapped to the upper arm of the person administering the injection;
   a coil spring disposed outside the cylinder and the glass tube and through which the piston rod extends, the spring urging the piston head away from the first end of the glass tube.

2. The syringe of claim 1 wherein the press handle is provided with two screws and the threaded wells therefor, one screw for blocking the second end of the conduit in the press handle and the other for storing the stuffing leaf when the syringe is used in the single injection mode.

* * * * *